(12) United States Patent
Kerr

(10) Patent No.: US 9,454,769 B2
(45) Date of Patent: Sep. 27, 2016

(54) COMMUNICATING A TARGETED MESSAGE TO A WIRELESS DEVICE BASED ON LOCATION AND TWO USER PROFILES

(71) Applicant: Michael A. Kerr, Reno, NV (US)

(72) Inventor: Michael A. Kerr, Reno, NV (US)

(73) Assignee: NEXRF CORPORATION, Reno, NV (US)

( * ) Notice: Subject to any disclaimer, the term of this patent is extended or adjusted under 35 U.S.C. 154(b) by 0 days.

(21) Appl. No.: 13/647,620

(22) Filed: Oct. 9, 2012

(65) Prior Publication Data

US 2014/0222569 A1 Aug. 7, 2014

Related U.S. Application Data

(63) Continuation of application No. 11/948,007, filed on Nov. 30, 2007, and a continuation-in-part of application No. 10/681,034, filed on Oct. 8, 2003, now Pat. No. 8,403,755, which is a continuation of application No. 09/899,559, filed on Jul. 5, 2001, now abandoned.

(60) Provisional application No. 60/872,351, filed on Nov. 30, 2006, provisional application No. 60/266,956, filed on Feb. 6, 2001.

(51) Int. Cl.
| | |
|---|---|
| *G06Q 30/02* | (2012.01) |
| *C07K 14/705* | (2006.01) |
| *G07F 17/32* | (2006.01) |
| *H04W 4/02* | (2009.01) |

(52) U.S. Cl.
CPC ......... *G06Q 30/0224* (2013.01); *C07K 14/705* (2013.01); *G07F 17/32* (2013.01); *G07F 17/3239* (2013.01); *H04W 4/02* (2013.01)

(58) Field of Classification Search
USPC .......................................... 463/39, 40, 42, 43
See application file for complete search history.

(56) References Cited

U.S. PATENT DOCUMENTS

| 4,339,798 A | 7/1982 | Hedges et al. |
| 4,856,787 A | 8/1989 | Itkis |

(Continued)

FOREIGN PATENT DOCUMENTS

| FI | WO2008065257 A1 | 6/2008 |
| JP | 2009025019 A | 2/2009 |

OTHER PUBLICATIONS

Wirelss Network. Wikipedia. http://en.wikipedia.org/wiki/Wireless_network. Nov. 17, 2008.

(Continued)

*Primary Examiner* — Paul A D'Agostino
*Assistant Examiner* — Brandon Gray
(74) *Attorney, Agent, or Firm* — Kerr IP Group, LLC; Michael A. Kerr

(57) ABSTRACT

A method for tracking patronage of a customer in at least one casino property is described. The method comprises monitoring a wireless handset that determines the location of the customer. The method then proceeds to generate a user profile that comprises user preferences and monitored betting activity associated with the customer and accumulated points stored in a customer account according to a monetary value of the monitored betting activity. Complementary goods or services are determined based on the accumulated points associated with the customer account. A message is sent to the wireless handset associated with the complementary goods or services that is consistent with the user preferences.

21 Claims, 2 Drawing Sheets

(56) References Cited

U.S. PATENT DOCUMENTS

| | | |
|---|---|---|
| 5,586,937 A | 12/1996 | Menashe |
| 5,594,491 A | 1/1997 | Hodge et al. |
| 5,630,757 A | 5/1997 | Gagin et al. |
| 5,643,086 A | 7/1997 | Alcorn et al. |
| 5,738,583 A | 4/1998 | Comas et al. |
| 5,761,416 A | 6/1998 | Mandal et al. |
| 5,761,647 A | 6/1998 | Boushy |
| 5,762,552 A | 6/1998 | Vuong et al. |
| 5,768,382 A | 6/1998 | Schneier et al. |
| 5,779,545 A | 7/1998 | Berg et al. |
| 5,800,268 A | 9/1998 | Molnick |
| 5,851,149 A | 12/1998 | Xidos et al. |
| 5,871,398 A | 2/1999 | Schneier et al. |
| 5,902,983 A | 5/1999 | Crevalt et al. |
| 5,947,821 A | 9/1999 | Stone |
| 5,971,849 A | 10/1999 | Falciglia |
| 6,001,016 A | 12/1999 | Walker et al. |
| 6,010,404 A | 1/2000 | Walker et al. |
| 6,106,396 A | 8/2000 | Alcorn et al. |
| 6,142,876 A | 11/2000 | Cumbers |
| 6,159,095 A | 12/2000 | Frohm et al. |
| 6,178,510 B1 | 1/2001 | O'Connor et al. |
| 6,203,428 B1 | 3/2001 | Giobbi et al. |
| 6,259,405 B1 | 7/2001 | Stewart et al. |
| 6,322,446 B1 | 11/2001 | Yacenda |
| 6,327,535 B1 | 12/2001 | Evans et al. |
| 6,409,602 B1 | 6/2002 | Wiltshire et al. |
| 6,500,068 B2 | 12/2002 | Walker et al. |
| 6,508,709 B1 | 1/2003 | Karmarkar |
| 6,508,710 B1 | 1/2003 | Paravia et al. |
| 6,527,638 B1 | 3/2003 | Walker et al. |
| 6,554,705 B1 | 4/2003 | Cumbers |
| 6,575,834 B1 | 6/2003 | Lindo |
| 6,606,494 B1 | 8/2003 | Arpee et al. |
| 6,612,928 B1 | 9/2003 | Bradford et al. |
| 6,628,939 B2 | 9/2003 | Paulsen |
| 6,638,170 B1 | 10/2003 | Crumby |
| 6,640,218 B1 | 10/2003 | Golding et al. |
| 6,676,522 B2 | 1/2004 | Rowe |
| 6,682,421 B1 | 1/2004 | Rowe et al. |
| 6,702,672 B1 | 3/2004 | Angell et al. |
| 6,709,333 B1 | 3/2004 | Bradford et al. |
| 6,709,631 B2 | 3/2004 | Mori et al. |
| 6,719,631 B1 | 4/2004 | Tulley et al. |
| 6,749,512 B2 | 6/2004 | MacGregor et al. |
| 6,782,253 B1 | 8/2004 | Shteyn et al. |
| 6,834,195 B2 | 12/2004 | Brandenberg et al. |
| 6,875,110 B1 | 4/2005 | Crumby |
| 6,879,838 B2 | 4/2005 | Rankin et al. |
| 6,884,162 B2 | 4/2005 | Raverdy et al. |
| 6,942,574 B1 | 9/2005 | LeMay et al. |
| 7,035,651 B2 | 4/2006 | Schreiner et al. |
| 7,076,243 B2 | 7/2006 | Parupudi et al. |
| 7,107,245 B1 | 9/2006 | Kowalick |
| 7,136,915 B2 | 11/2006 | Rieger, III |
| 7,196,662 B2 | 3/2007 | Misikangas et al. |
| 7,209,752 B2 | 4/2007 | Myllymaki et al. |
| 7,213,048 B1 | 5/2007 | Parupudi et al. |
| 7,218,941 B1 | 5/2007 | Kubo et al. |
| 7,228,136 B2 | 6/2007 | Myllymaki et al. |
| 7,299,059 B2 | 11/2007 | Misikangas et al. |
| 7,338,372 B2 | 3/2008 | Morrow et al. |
| 7,341,522 B2 | 3/2008 | Yamagishi |
| 7,349,683 B2 | 3/2008 | Misikangas et al. |
| 7,359,714 B2 | 4/2008 | Parupudi et al. |
| 7,397,424 B2 | 7/2008 | Houri |
| 7,450,954 B2 | 11/2008 | Randall |
| 7,493,565 B2 | 2/2009 | Parupudi et al. |
| 7,529,639 B2 | 5/2009 | Rasanen et al. |
| 7,534,169 B2 | 5/2009 | Amaitis et al. |
| 7,611,407 B1 | 11/2009 | Itkis et al. |
| 7,753,772 B1 | 7/2010 | Walker et al. |
| 8,002,617 B1 | 8/2011 | Uskela et al. |
| 8,029,349 B2 | 10/2011 | Lind |
| 8,172,684 B2 | 5/2012 | Adiraju et al. |
| 8,403,755 B2 | 3/2013 | Kerr |
| 8,492,995 B2 | 7/2013 | Maxik et al. |
| 8,506,406 B2 | 8/2013 | Kerr |
| 8,506,407 B2 | 8/2013 | Kerr |
| 8,523,679 B2 | 9/2013 | Kerr |
| 8,738,024 B1 | 5/2014 | Kerr et al. |
| 8,747,229 B2 | 6/2014 | Kerr |
| 8,942,995 B1 | 1/2015 | Kerr |
| 9,043,222 B1 | 5/2015 | Kerr et al. |
| 2001/0004768 A1 | 6/2001 | Hodge et al. |
| 2001/0005908 A1 | 6/2001 | Hodge et al. |
| 2001/0036224 A1* | 11/2001 | Demello et al. ............... 375/220 |
| 2001/0039210 A1 | 11/2001 | St-Denis |
| 2001/0044337 A1 | 11/2001 | Rowe et al. |
| 2002/0002073 A1 | 1/2002 | Montgomery et al. |
| 2002/0007494 A1 | 1/2002 | Hodge |
| 2002/0056125 A1 | 5/2002 | Hodge et al. |
| 2002/0056143 A1 | 5/2002 | Hodge et al. |
| 2002/0069105 A1* | 6/2002 | do Rosario Botelho et al. ............... 705/14 |
| 2002/0077130 A1* | 6/2002 | Owensby ...................... 455/466 |
| 2002/0077167 A1 | 6/2002 | Merari |
| 2002/0091568 A1 | 7/2002 | Kraft et al. |
| 2002/0103028 A1 | 8/2002 | Carter et al. |
| 2002/0111210 A1 | 8/2002 | Luciano et al. |
| 2002/0111907 A1 | 8/2002 | Ling |
| 2002/0133707 A1* | 9/2002 | Newcombe ................... 713/183 |
| 2002/0142815 A1 | 10/2002 | Candelore |
| 2002/0142844 A1 | 10/2002 | Kerr |
| 2002/0142846 A1 | 10/2002 | Paulsen |
| 2002/0144151 A1 | 10/2002 | Shell et al. |
| 2002/0174436 A1* | 11/2002 | Wu et al. ......................... 725/87 |
| 2002/0198775 A1 | 12/2002 | Ryan |
| 2003/0009385 A1* | 1/2003 | Tucciarone et al. ............ 705/26 |
| 2003/0030666 A1 | 2/2003 | Najmi et al. |
| 2003/0032409 A1 | 2/2003 | Hutcheson et al. |
| 2003/0064805 A1 | 4/2003 | Wells |
| 2003/0144017 A1* | 7/2003 | Inselberg ...................... 455/517 |
| 2004/0023721 A1 | 2/2004 | Giobbi |
| 2004/0192438 A1 | 9/2004 | Wells et al. |
| 2004/0224757 A1 | 11/2004 | Yamamura et al. |
| 2005/0046608 A1 | 3/2005 | Schantz et al. |
| 2005/0048990 A1 | 3/2005 | Lauriol |
| 2005/0085257 A1 | 4/2005 | Laird et al. |
| 2005/0114212 A1 | 5/2005 | Carrez et al. |
| 2005/0136949 A1 | 6/2005 | Barnes |
| 2005/0154646 A1 | 7/2005 | Chermesino |
| 2005/0159883 A1 | 7/2005 | Humphries et al. |
| 2005/0181804 A1 | 8/2005 | Misikangas et al. |
| 2005/0246334 A1 | 11/2005 | Tao et al. |
| 2005/0261063 A1 | 11/2005 | Boyd et al. |
| 2006/0003830 A1 | 1/2006 | Walker et al. |
| 2006/0004627 A1 | 1/2006 | Baluja |
| 2006/0058102 A1 | 3/2006 | Nguyen et al. |
| 2006/0063575 A1 | 3/2006 | Gatto et al. |
| 2006/0125693 A1 | 6/2006 | Recker |
| 2006/0181411 A1 | 8/2006 | Fast et al. |
| 2006/0189382 A1 | 8/2006 | Muir et al. |
| 2006/0194633 A1 | 8/2006 | Paulsen |
| 2006/0238382 A1 | 10/2006 | Kimchi et al. |
| 2006/0240891 A1 | 10/2006 | Klinkhammer et al. |
| 2006/0287810 A1 | 12/2006 | Sadri et al. |
| 2007/0008108 A1 | 1/2007 | Schurig et al. |
| 2007/0024580 A1 | 2/2007 | Sands et al. |
| 2007/0025265 A1 | 2/2007 | Porras et al. |
| 2007/0060306 A1 | 3/2007 | Amaitis et al. |
| 2007/0061229 A1 | 3/2007 | Ramer et al. |
| 2007/0087834 A1 | 4/2007 | Moser et al. |
| 2007/0100963 A1 | 5/2007 | Ban et al. |
| 2007/0136132 A1 | 6/2007 | Weiser et al. |
| 2007/0149215 A1 | 6/2007 | Misikangas |
| 2007/0149216 A1 | 6/2007 | Misikangas |
| 2007/0167210 A1 | 7/2007 | Kelly et al. |
| 2007/0168127 A1 | 7/2007 | Zaruba et al. |
| 2007/0184852 A1 | 8/2007 | Johnson et al. |
| 2007/0218975 A1 | 9/2007 | Iddings et al. |
| 2007/0243925 A1 | 10/2007 | LeMay et al. |
| 2007/0244633 A1 | 10/2007 | Phillips et al. |
| 2007/0257831 A1 | 11/2007 | Mathews et al. |

(56) References Cited

U.S. PATENT DOCUMENTS

| | | |
|---|---|---|
| 2007/0270212 A1 | 11/2007 | Cockerille et al. |
| 2007/0281692 A1 | 12/2007 | Bucher et al. |
| 2008/0026844 A1 | 1/2008 | Wells |
| 2008/0032705 A1 | 2/2008 | Patel et al. |
| 2008/0039192 A1 | 2/2008 | Laut |
| 2008/0057894 A1 | 3/2008 | Aleksic et al. |
| 2008/0076572 A1 | 3/2008 | Nguyen et al. |
| 2008/0085692 A1 | 4/2008 | Hart et al. |
| 2008/0096659 A1 | 4/2008 | Kreloff et al. |
| 2008/0097858 A1 | 4/2008 | Vucina et al. |
| 2008/0102947 A1 | 5/2008 | Hays et al. |
| 2008/0108430 A1 | 5/2008 | Evans |
| 2008/0113785 A1 | 5/2008 | Alderucci et al. |
| 2008/0153515 A1 | 6/2008 | Mock et al. |
| 2008/0162037 A1 | 7/2008 | Hasan |
| 2008/0166973 A1 | 7/2008 | Hart et al. |
| 2008/0167106 A1 | 7/2008 | Lutnick et al. |
| 2008/0186234 A1 | 8/2008 | Alles et al. |
| 2008/0189360 A1 | 8/2008 | Kiley et al. |
| 2008/0207296 A1 | 8/2008 | Lutnick et al. |
| 2008/0227473 A1 | 9/2008 | Haney |
| 2008/0249833 A1 | 10/2008 | Ali et al. |
| 2008/0252527 A1 | 10/2008 | Garcia |
| 2008/0281668 A1 | 11/2008 | Nurminen |
| 2009/0018929 A1 | 1/2009 | Weathers |
| 2009/0150217 A1 | 6/2009 | Luff |
| 2009/0197684 A1 | 8/2009 | Arezina et al. |
| 2009/0213771 A1 | 8/2009 | Celentano et al. |
| 2009/0214036 A1 | 8/2009 | Shen et al. |
| 2009/0298513 A1 | 12/2009 | Hampel et al. |
| 2010/0022308 A1 | 1/2010 | Hartmann et al. |
| 2010/0027521 A1 | 2/2010 | Huber et al. |
| 2010/0039929 A1 | 2/2010 | Cho et al. |
| 2010/0048242 A1 | 2/2010 | Rhoads et al. |
| 2010/0063854 A1 | 3/2010 | Purvis et al. |
| 2010/0121567 A1 | 5/2010 | Mendelson |
| 2010/0167771 A1 | 7/2010 | Raghothaman et al. |
| 2010/0179885 A1 | 7/2010 | Fiorentino |
| 2010/0280960 A1 | 11/2010 | Ziotopoulos et al. |
| 2010/0287033 A1 | 11/2010 | Mathur |
| 2010/0302056 A1 | 12/2010 | Dutton et al. |
| 2010/0305855 A1 | 12/2010 | Dutton et al. |
| 2010/0331016 A1 | 12/2010 | Dutton et al. |
| 2011/0078167 A1 | 3/2011 | Sundaresan et al. |
| 2011/0103360 A1 | 5/2011 | Ku et al. |
| 2012/0115512 A1 | 5/2012 | Grainger et al. |
| 2012/0122476 A1 | 5/2012 | Lee et al. |

OTHER PUBLICATIONS

"Tracking Cookie." Wikipedia. http://en.wikipedia.org/wiki/Tracking_cookie. May 24, 2009.
Blom et al. "Transmission Power Measurements for Wireless Sensor Nodes and their Relationship to Battery Level." Symposium on Wireless Communication Systems. pp. 342-345, Sep. 7, 2005.
"Wi-Fi Location-Based Services—Design and Deployment Considerations." 2006 Cisco Systems. Accessed Dec. 2008. https://learningnetwork.cisco.com/docs/DOC-3418.
"Location in SIP/IP Core Architecture." Open Mobile Alliance. Sep. 4, 2008. Accessed Dec. 2008. http://www.openmobilealliance.org/technical/release_program/locsip_archive.aspx.
Want et al. "The Active Badge Location System." ACM Transactions on Office Information Systems (TOIS) vol. 10. No. 1, pp. 91-102, Jan. 1992.
Youssef et al. "Location-Clustering Techniques for WLAN Location Determination Systems." 2006. http://wrc.ejust.edu.eg/papers/ijca.pdf.
Vegni et al. "Local Positioning Services on IEEE 802.11 Networks." Radio Engineering, pp. 42-47, vol. 17, No. 2, Jun. 2008.
Ladd et al. "On the Feasibility of Using Wireless Ethernet for Indoor Localization." IEEE Transactions on Robotics and Automation, pp. 555-559, vol. 20, Issue 3, No. 3, Jun. 2004.
Ladd et al. "Using Wireless Ethernet for Localization." IEEE/RJS International Conference on Intelligent Robots and Systems. 2002.
Kitasuka et al. "Positioning Technique of Wireless LAN Terminal Using Rssi between Terminals". Jun. 2005. Accessed Dec. 2008. http://www.techrepublic.com/whitepapers/positioning-technique-of-wireless-lan-terminals-using-rssi-between-terminals/330959.
Lafargue, Edouard. "Wireless Network Audits using Open Source Tools". SANS Institute 2003. Accessed Dec. 2008. http://www.sans.org/reading_room/whitepapers/auditing/wireless-network-audits-open-source-tools_1235.
Heidari, Mohannad. "A Testbed for Real-Time Performance Evaluation of RSS-Based Indoor Geolocation Systems in a Laboratory Environment". Apr. 21, 2005. Accessed Dec. 2008. https://www.wpi.edu/Pubs/ETD/Available/etd-050407-112549/unrestricted/massad.pdf.
Li et al. "A New Method for Yielding a Database of Location Fingerprints in WLAN" IEE Communications Proceedings, pp. 580-586, vol. 152, Issue 5, Oct. 7, 2005.
Sakata et al. "An efficient algorithm for Kriging approximation and optimization with large-scale sampling data". Computer Methods in Applied Mechanics and Engineering. vol. 193, Issues 3-5, pp. 385-404, Jan. 23, 2004.
Muthukrishnan, et al. "Sensing motion using spectral and spatial analysis of WLAN RSSI." Proceedings of the 2nd European conference on Smart sensing and context. 2007. pp. 62-76.
Capkun et al. "Mobility Helps Peer-to-Peer Security." IEEE Transactions on Mobile Computing. vol. 5, Issue 1, pp. 43-51, Jan. 2006.
Milojicic et al. "Peer-to-Peer Computing" Jul. 10, 2002. https://www.hpl.hp.com/techreports/2002/HPL-2002-57R1.pdf.
"The New Normal of Retailing: The Rise of the Mobile Shopper." Next Generation Retail Summit. 2010. http://www.ngrsummit.com/media/whitepapers/Microsoft_NGRUS.pdf.
Lamarca et al. "Place Lab: Positioning Using Radio Beacons in the Wild." Pervasive 2005, LNCS 3468, pp. 116-133, 2005.
Borriello et al. "Delivering Real-World Ubiquitous Location Systems." Communications of the ACM. pp. 36-41, vol. 48, Issue 3, Mar. 2005.
Schilit et al. "Challenge: Ubiquitous Location-Aware Computing and the "Place Lab" Initiative." WMASH Proceedings of the 1st ACM International Workshop on Wireless Mobile Applications and Services on WLAN Hotspots. 2003.
Hightower et al. "Practical Lessons from the Place Lab." IEEE Pervasive Computing. pp. 32-39, vol. 5, Issue 3, Jul.-Sep. 2006.
Hile et al. "Indoor Location Estimation with Placelab." http://www.cs.washington.edu/education/courses/cse590gb/04wi/projects/hile-liu/. Jan. 8, 2004. Accessed on Sep. 5, 2008.
Kang "Extracting Places from Traces of Locations." ACM SIGMOBILE Mobile Computing and Communications Review. vol. 9, Issue 3, Jul. 2005.
Lamarca et al. "Self-Mapping in 802.11 Location Systems." UbiComp 2005: Ubiquitous Computing Lecture Notes in Computer Science, 2005, vol. 3660/2005, 903, DOI: 10.1007/11551201_6.
Otsason et al. "Accurate GSM Indoor Localization." Ubiquitous Computing 2005, LNCS 3660, pp. 141-158, 2005.
Chen et al. "Practical Metropolitan-Scale Positioning for GSM Phone." UbiComp 2006: Ubiquitous Computing Lecture Notes in Computer Science, 2006, vol. 4206/2006, pp. 225-242.
Varshavsky et al. "Are GSM Phones THE Solution for Localization?" 7th IEEE Workshop on Mobile Computing Systems and Applications, 2006. pp. 34-42, Aug. 1, 2005.
Chawathe et al. "A Case Study in Building Layered DHT Applications." Proceedings of the 2005 conference on Applications, technologies, architectures, and protocols for computer communications. vol. 35, Issue 4, Oct. 2005.
Lamarca et al. "Finding Yourself: Experimental location technology relies on Wi-Fi and cellphone signals instead of orbiting satellites." Dec. 2004. http://spectrum.ieee.org/computing/networks/finding-yourself.
Letchner et al. "Large-Scale Localization from Wireless Signal Strength." In Proceedings of the National Conference on Artificial Intelligence (AAAI), 2005.

(56) References Cited

OTHER PUBLICATIONS

Welbourne et al. "Mobile Context Inference Using Low-Cost Sensors." Location and Context-Awareness Lecture Notes in Computer Science, 2005, vol. 3479/2005, pp. 95-127.

Balakrishnan et al. "Lessons from Developing and Deploying the Cricket Indoor Location System." Nov. 7, 2003. http://www.sds.lcs.mit.edu/projects/cricket/V1Exp.pdf.

Cheng et al. "Accuracy Characterization for Metropolitan-scale Wi-Fi Localization." Proceedings of the 3rd international conference on Mobile systems, applications, and services. 2005.

"Ekahau Positioning Engine 4.2." 2008. http://www.nowire.se/images/produktblad/ekahau/datasheet_epe_42_en_11022008_lo.pdf. Sep. 29, 2008.

"Internet Industry Interacting Gambling Code: A Code for Industry Co-Regulation in the Area of Internet Gambling Content Pursuant to the Requirements of the Interactive Gaming Act of 2001". Internet Industry Association. Dec. 2001.

"Wireless Network." Wikipedia. http://en.wikipedia.org/wiki/Wireless.sub.--network. Nov. 17, 2008.

HTTP Cookie, redirected from tracking cookie as downloaded from wikipedia, 41 pages.

Wireless Network as downloaded from wikipedia.com, pages. 5 pages.

\* cited by examiner

COMMUNICATING A TARGETED MESSAGE TO A WIRELESS DEVICE BASED ON LOCATION AND TWO USER PROFILES

CROSS REFERENCE

This patent application is a continuation of U.S. patent application Ser. No. 11/948,007, filed Nov. 30, 2007, which claims priority to Provisional Application No. 60/872,351, filed Nov. 30, 2006; and is a continuation-in-part of U.S. patent application Ser. No. 10/681,034, filed Oct. 8, 2003, which is a continuation of U.S. patent application Ser. No. 09/899,559, filed Jul. 5, 2001 (now abandoned), which claims priority to Provisional Application No. 60/266,956, filed Feb. 6, 2001; all of which are hereby incorporated by reference.

FIELD OF THE INVENTION

This invention relates to player tracking using a wireless communication device for a casino property. More particularly, the invention relates to sending messages to wireless devices based on user preferences, location, and player tracking information.

BACKGROUND

Generally, present day player tracking systems rely on the use of mag stripe cards. Currently, wireless devices are being promoted that perform various player tracking functions. However, these wireless devices are generally limited to being used exclusively on the casino floor for wireless gaming. These wireless devices are not enabled to take advantage of the player's mobility in the casino megaplex or similar large entertainment property.

SUMMARY

A system and method for communicating a targeted message to a particular user located on a property is described. The method includes gathering a first user profile associated with the user, wherein the first user profile is controlled by the property. The method then proceeds to gather a second user profile that is generated by the user. The first user profile and second user profile are then authenticated. A wireless communication device then communicates with a user profile server that accesses the first user profile. The user accessing the wireless communication device and can then opt-in to provide location information to a location server. A software program is then downloaded to the wireless communication device. The second server monitors the wireless device and determines the location of the device. The wireless device is configured to communicate with a network using at least one wireless networking protocol. A message is sent to the wireless communication device based on the location of the user, the first user profile controlled by the property, and the second user profile determined by the user.

A system for communicating a targeted message to a particular user located on a property is also described. The system includes a first user profile, a second user profile, a wireless communication device, a user opt-in, a software program, a user profile server, a location server and a message sent to the wireless communication device. The first user profile is associated with the particular user and is controlled by the property. The second user profile is generated directly by the particular user. The wireless communication device corresponds to the user. The user opt-in enables the user to provide location information to the location server. The user opt-in is communicated from the wireless communication device and the software program is downloaded to the wireless communication device. The wireless communication device communicates location information about the user to the location server by accessing a network using a wireless networking protocol. The user profile server accesses the first user profile controlled by the property. The message is sent to the wireless communication device based on the location of user, the first user profile determined by the property, and the second user profile determined by the user.

In one illustrative embodiment, the targeted message is a coupon. The coupon sent to the wireless communication device based on the location of user, the first user profile determined by the property, and the second user profile determined by the user. The illustrative coupon is sent to the wireless communication device when the wireless communication device is inside a store.

DRAWINGS

The present invention will be more fully understood by reference to the following drawings which are for illustrative, not limiting, purposes.

DETAILED DESCRIPTION

Figure 1:
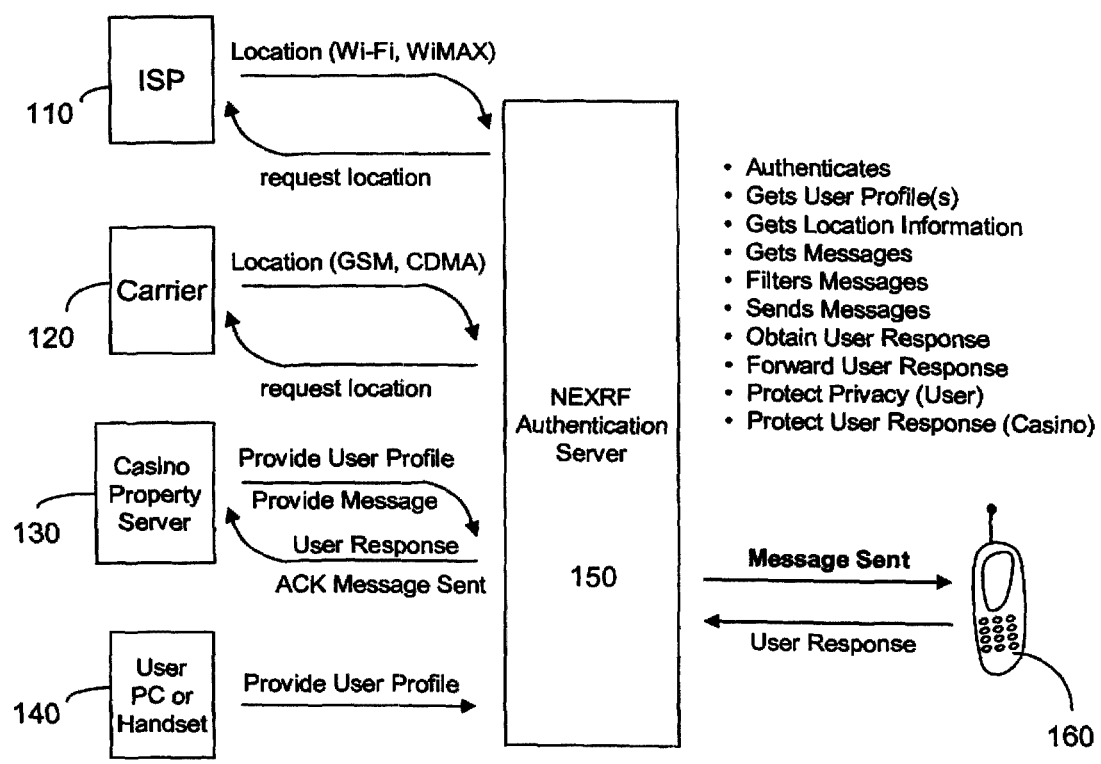
FIG. 1 shows an illustrative client-server system for player tracking using a wireless communication device.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and apparatus described hereinafter may vary as to configuration and as to details. Additionally, the method may vary as to details, order of the actions, or other variations without departing from the illustrative method disclosed herein.

The conversion of a wireless communication device such as a mobile handset to a software valet that is at the beck and call of the user is described. Note, the terms wireless communication device and mobile handset are used interchangeably. Ideally, the solution is hardware agnostic, so the wireless communication device may be a mobile phone, a mobile Wi-Fi handset, or a WiMAX handset. The goal is to provide an integrated platform that supports the personalization of data flow for a wireless communication device. The illustrative application is targeted messaging as a function of the user profile, user location, and time. The user profile includes a plurality of user preferences such as dining preferences, entertainment preferences, drink preferences, and other such personalized preferences.

The solution supports target advertisements, personalization, and permits a handset to "close the transactional loop" where the mobile handset becomes a Point-of-Sale (POS) device.

The mobile handset which performs the operations described above may be used to support mobile gaming transactions within a casino environment, support secure lottery based transactions, or similar gaming related activities. Thus, the mobile handset can also be converted into a secure gaming device, and the description provided in the patent application entitled BIOMETRIC BROADBAND GAMING SYSTEM AND METHOD filed in 2001 by the same named inventor, which is hereby incorporated by reference to describe a networked server based gaming system.

The wireless communication device may be a mobile handset, mobile phone, wireless phone, portable cell phone, cellular phone, portable phone, a personal digital assistant (PDA), or any type of mobile terminal which is regularly carried by a user and has all the elements necessary for operation in a wireless communication system. The wireless communications include, by way of example and not of limitation, CDMA, WCDMA, GSM or UMTS or any other wireless communication system such as wireless local area network, WLAN, Wi-Fi or WiMAX. It shall be appreciated by those of ordinary skill in the art that the term wireless communication device, mobile handset, wireless phone, and mobile phone are interchangeable.

The wireless communication device is in communication with an antenna. The antenna may be one of a plurality of base station antennas associated with a cellular phone network, or an antenna associated with wireless local area network access point, and may use Wi-Fi or Wi MAX, or other such networking protocols.

The goal of a casino property is to keep players on the property, keep players busy gambling, and get players back on the property. The illustrative service offering is integrated into a wireless communication device that may be provided as a complimentary service to the player. The wireless communication device provides the well-known service offerings of a cell phone. Additionally, the wireless communication device is programmed to receive a variety of messages with user-specific information, such as preferred gaming experience, food preferences, and other specific offerings associated with the individual. Thus, if the prospective player is off the casino property, a targeted desirable message is sent, e.g. "Limo is waiting with front row tickets for Van Morrison. Respond if you want to see show." If the user responds with a "yes," a ticket or other means for authorizing entry to the show is sent to the handset.

Note that the player or player tracking solution can also be used to support wireless gaming such as a sports book, horse racing, bingo, slots, and even table games.

The cross-over applications for the illustrative solution are established by using the illustrative solution to communicate targeted advertising or messages and to facilitate transactions, such as gift card transactions, loyalty transactions, coupon based transactions and similar small transactions, i.e.\ transactions less than $10. The user profile is used to filter messages and to perform mobile commerce transactions. The location information can be used to detect and prevent fraud, and the transactional size minimizes the impact of fraud.

In the illustrative embodiment, a targeted message is sent to a user, and then a transaction may be facilitated with the message or advertisement. Preferably, the user profile remains secure and in control of the user. The user profile filters information on behalf of the user, so that only desirable content is received. The advertisements are managed and controlled so that they conform to local laws.

For utility and/or process engineering applications, one sample application is securely sending automated messages that are triggered by sensor outputs and location, e.g. wireless telemetry to an affordable wireless communication device. For example, in certain high risk working environments such as nuclear power plants, oil well platforms, or oil refineries, there is a need to provide individuals with real-time alarm data that is location specific. This illustrative solution supports sending these targeted messages as a function of location, time and sensor input to an affordable handset leveraging an existing wireless network infrastructure.

Another industrial application includes regulatory applications such as environmental monitoring. With the described solution all that is needed is a wireless communication device or PC card that is in communication with a sensor network. Data can be securely accessed from any networked device. User profiles can be created that filter content, so a first set of information is available to the regulatory agency, a second set of information is available to offsite personnel or consultants and a third set of information is available to on-site personnel handling day-to-day activities.

Finally, the illustrative solution can support a military application that prevents "friendly fire" casualties because messages can be sent on a real-time basis as function of the user location, regardless of the type of wireless network. The illustrative solution resides on an affordable wireless communication device that securely identifies location, and can be used to validate that a particular user is NOT an enemy combatant.

In a first illustrative embodiment, the solution is embodied in a client server architecture as described in FIG. 1. The client-server system model is scalable, and supports multiple clients and servers.

In FIG. 1, the location information is collected from an ISP 110 and/or a Carrier 120. The collection of location information is feasible if authorized by the user. If for instance the "user" is a casino property that is loaning the wireless communication device 160 to a casino guest, then the casino property may elect to have the location information for the wireless communication device 160 available to an authorized entity such as the intermediary server 150. In an alternative embodiment, where the owner of the handset 160 is the casino guest, the casino guest opts-in to provide location information to the intermediary server 150 based on the user profile submitted by the casino guest and downloads the software program that mirrors the operations performed by the casino property's wireless communication device.

The illustrative ISP 110 provides wireless connectivity using one of a plurality of networking standards such as Wi-Fi or WiMAX. The ISP 110 is configured to identify the location of the wireless communication device 160 using well known location based techniques such as triangulation, GPS, and other such methods. The illustrative Carrier 120 that provides wireless services must comply with the E911 regulations and also generates location information. This location information is served by the ISP 110 or Carrier 120 to the intermediary server 150.

A variety of different user profiles may be collected from different sources. For simplicity, a first user profile is collected from a casino property, and a second user profile is collected directly from the user. In the casino generated user profile, the casino may indicate user preferences such as cocktail preferences and dining preferences. The casino user profile may comprise monitored betting activity associated with the player and accumulated points stored in a player account according to a monetary value of the monitored betting activity. Complementary goods or services are determined based on the accumulated points associated with the player account, and a message may be sent to the wireless communication device 160 associated with the complementary goods or services that are consistent with the user profile. The casino user profile can also be used as a basis to provide mobile concierge services.

The second user profile may be generated separately by a player using a personal computer (PC) 140 and may indicate the user's "comp" preferences where the player may prefer to obtain tickets to a particular Vegas show and to opt-out of receiving comps for a particular dining establishment.

The intermediary server 150 authenticates information that is received from each source. The intermediary server 150 gathers the user profile information including user preferences and obtains the location information. Additionally, the intermediary server 150 receives the messages, which are to be sent to the user as a function of the user profile, location, and time. The illustrative messages are generated by the illustrative casino property; however, the content may be generated by any other entity identified by the user's particular profile. An intelligent agent or "virtual" agent is generated based on the one or more user profiles, and messages are filtered according to the user preferences that are embodied in an agent's requirements. Filtered messages are then sent to the wireless communication device 160.

The intermediary server 150 then waits for a user response. The user response may be positive and the user may wish to proceed with obtaining more information or acknowledging a particular action. The user may also NOT like the message sent, and the user response may be an opt-out request that states this message is undesirable. Alternatively, the user may provide a "thumbs up" or "thumbs down" feedback. Regardless, the resulting response is sent to the casino server 130. The user profile resident on the intermediary server 150 is updated based on the user response.

In an alternative embodiment, the functions of the casino property server 130 and the authentication server 150 are performed on a single server for either a brick-and-mortar casino property or for a web-based casino property. If the intermediary server 150 resides on the casino property, privacy laws may be impacted because of perceived overreaching by the casino property because it warehouses location information. However, anonymity may not be an issue in certain foreign jurisdictions.

Although there a numerous benefits in the client-server architecture, there are also limitations associated with the client-server architecture that are not overcome by distributed object computing. These limitations include cost, lack of scalability, a single point of failure, administration difficulties, and the inefficient use of network resources. The peer-to-peer architecture is intended to address the limitations of the client-server solution and a migration from the client-server solution to the P2P solution is anticipated. In a peer-to-peer architecture clients are also servers and routers. Additionally, each node contributes content, storage, memory, and processing resources. The network is dynamic and nodes are free to enter and exit the network. The nodes can also collaborate directly with one another. Furthermore, nodes can have varying capabilities.

The goals and benefits of peer-to-peer systems include efficient use of resources so unused bandwidth, storage, and processing power at the edge of the network can be used efficiently. P2P systems are also scalable because there is no central information, communication and computation bottleneck. The P2P systems are also reliable and provide no single point of failure. There is also an ease of administration because the nodes self-organize and have built-in fault tolerance, replication, and load balancing, resulting in increased autonomy. Since a P2P network is not a centralized system, there a greater degree of anonymity and privacy in a P2P network. Since the P2P environment is highly dynamic, ad hoc communication and collaboration is supported.

Figure 2:
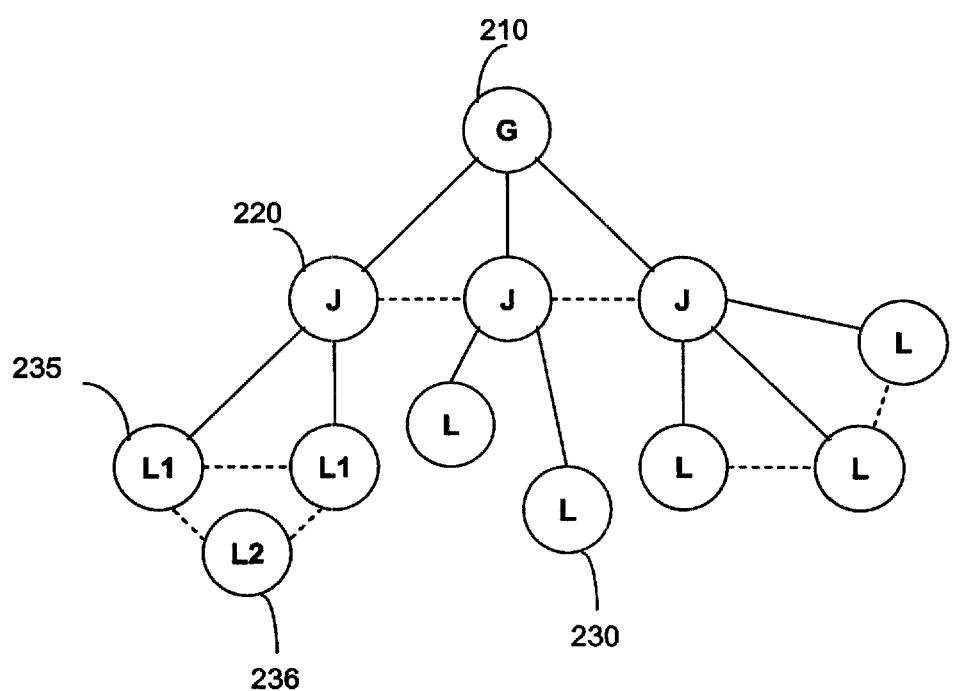
FIG. 2 shows an illustrative peer-to-peer system for player tracking using a wireless communication device.

Referring to FIG. 2 there is shown an illustrative hierarchical P2P network which provides a second illustrative embodiment. For the illustrative P2P embodiment, the illustrative embodiment is a hierarchical peer-to-peer network that is comprised of three different types of nodes: Global Node(s) 210, Jurisdictional Node(s) 220, and Local Node(s) 230. There may be different levels or subsets for each type of node, e.g. L 1 235 and L2 236. The hierarchical peer-to-peer network overlay is highly scalable, robust, and secure. The P2P overlay resides on a group of personal computers or servers, and leverages resources within an existing network infrastructure.

The development of the user profile including the user preferences and monitored betting activity or "personalization" is performed and controlled by the user (or the casino property). Thus, the user profile remains resident on the wireless communication device or personal computer that is used to access the illustrative network. By having users control their own profiles, the user ensures that desirable messages are received.

The Global Node (G) 210 authenticates each node in the network including the Jurisdictional Node 220 and the L 1 235 and L2 236 Local Nodes. Additionally, the Global Node 210 authenticates the user accessing the network. The Global Node 210 provides oversight for the operations performed by each Jurisdictional Node 220. The Global Node 210 also ensures that the files being shared by each node have the stated content. The Global Node 210 combines the user profile information received from the L 1 nodes 235, the L2 nodes 236, and Jurisdictional Nodes 220 and generates a virtual agent. The virtual agent then filters information, and sends the filtered information to the L2 node 236, e.g. the user's wireless communication device 160.

In one embodiment where the user's privacy concerns are a high priority, the Global Node 210 performs the operations of an anonymizing proxy, so the user, the user profile and the wireless communication device 160 become anonymous. In another embodiment where the systems' security concerns are the highest priority, the Global Node 210 provides oversight for the operations performed by the L 1 235 and L2 236 nodes and anonymizing services are not performed.

In the illustrative P2P embodiment, the user profile is generated from information provided by the store (L 1 node 235), and the user (L2 node 236). Also, information may be provided from the Jurisdictional Node 220. Additionally, logged user profiles from a search engine may be used to contribute to the user profile. Although information from the Jurisdictional Node 220 and the logged search profiles from the user may contribute to the virtual agent, these contributions may conflict with the expectations of the store (L 1 node 235) and the user (L2 node 236).

For example, a store may not want to enable a user to perform a search for a particular item being sold at a store, thus the store may want to block searches on Google while the user is within the store. The store may achieve this goal if the store can convince the Jurisdictional Node 220 that specific search engines are to be blocked while the user is within the store. Note, the store can itself become a Jurisdictional Node 220 if the store provides in-store Wi-Fi access. The user can elect to circumvent this blocking by using the anonymizing services provided by the Global Node 210. However, these anonymizing services may not permit the user to obtain the same rebates or coupons as the user could obtain if the user elected not to be anonymous. Regardless of the situation, the user, the store, and possibly even the Carrier 120/ISP 110 determine the scope of their relationship, and P2P architecture simply facilitates building this relationship.

The illustrative Global Node 210 may also be configured to share transactional revenues with Jurisdictional Nodes 220 and Local Nodes 230 that contribute to the transaction. Completed Point-of-Sale (POS) transactional information may also be shared.

The Jurisdictional Node (J) 220 controls access to the network. The Jurisdictional Node 220 may be associated with an illustrative Carrier 120, service provider, or casino property. The Jurisdictional Node 220 pushes personalized data to the user based on the user's profile. The Jurisdictional Node 220 also polices the activities of each Local Node 230 within its network, and if a local node 230 is generating inappropriate content, the infected Local Node(s) 230 having the inappropriate content is blocked by the Jurisdictional Node 220. Additionally, the Jurisdictional Node 220 may have stored or generated user-specific information that it is willing to "share" with the Global Node 210 so that a "better" virtual agent can be generated on behalf of the user.

The Jurisdictional Node (J) 220 controls access to the network. The Jurisdictional Node 220 is associated with an illustrative Carrier 120 or service provider 110. The Jurisdiction Node 220 pushes personalized data to the user based on the user's profile. The Jurisdictional Node 220 also polices the activities of each Local Node 230 within its network, and if a local node 230 is generating inappropriate content, the infected Local Node(s) 230 having the inappropriate content is blocked by the Jurisdictional Node 220. Additionally, the Jurisdictional Node 220 may have stored or generated user-specific information that it is willing to "share" with the Global Node 210 so that a "better" virtual agent can be generated on behalf of the user.

Jurisdictional Node 220 tools may be licensed to the Carrier 120 and/or service provider 110. The tools permit the Jurisdictional Node 220 to generate revenue from sharing user profile information and from converting the wireless communication device to a Point-of-Sale (POS) device.

The Local Node (L) 230 stores the content that is sent via a targeted message. The local nodes 230 either provide or receive location information associated with the wireless communication device 160. There are two types of local nodes: the L 1 Node 235 is a store-centric node; and the L2 Node 236 is user-centric.

The L2 Node 236 (user) is associated with the user and may reside on the users' PC 140 and/or the users wireless communication device 160. The L2 Node 236 is configured to receive user profile information such as dining preferences, banking preferences, shopping preferences, in-store preferences, and opt-out preferences. For example, an opt-out preference may be "Block ALL Starbucks Messages." Additionally, the L2 Node 236 (user) may receive location information and permits users to communicate location information.

Additionally, the L2 Node 236 (user) may convert the wireless communication device 160 to a Point-of-Sale (POS) device that can use coupons, rebates, and gift cards. The L2 Node 236 (user) is configured to close the transactional loop after receiving a targeted message and completes a transaction associated with the targeted message.

The L 1 Node 235 (store) may also have user profile information that it would like to contribute to generate the localized targeted advertisement. The Local Nodes 230 store content is associated with a particular location. For example, the L 1 Node 235 (store) may store indoor and outdoor advertising messages, so one message is received in a parking lot and another message is received within the store.

The L 1 Node 235 (store) software enables the store to generate mobile advertisements for handsets and to share the store's user profile. Additionally, the software enables the store to convert the wireless communication device to a POS device is also provided.

The L2 Node 236 (user) software is freely distributed, unless the L2 Node 236 (user) software is used for industrial and/or military applications. For industrial and/or military applications, the entire hierarchical P2P network overlay will likely operate within a single organizational structure.

Casino Application

The casino application may reside in either the client-server network architecture or the P2P network architecture. However, because of the degree of control need over sensitive player information and because of the progression towards server based gaming, the client-server network architecture is likely the preferred architecture.

Player tracking is an important element of a casino property's goal to retain players and build player goodwill. Player tracking information is information related to how a player wagers in a casino property. Based on the player tracking information, the casino determines how to "comp" the player. Comps are complimentary gifts or services that are provided to the player, e.g. gaming credits, redeemable cash, free rooms, room upgrades, tickets to shows, show upgrades, complimentary restaurant meals, etc. Player tracking information is extremely sensitive and proprietary information that a casino property does NOT share with any competitors. Currently, player tracking is used to track "regular players" and usually a regular player is provided with a mag stripe card that the player swipes into a gaming machine or gives the dealer at a table game their card.

In a first casino property embodiment, the player is provided with a mobile handset that is GPS and/or location enabled. For illustrative purposes only, the player is a "whale" or high roller. The handset may provide local anonymity and the same benefits of an in-room phone. In a second casino property embodiment, the player provides a phone number, and allows one or more software applets to be downloaded to their handset.

Casino properties maintain profiles for their preferred players. These profiles are used to create an experience that keeps the player coming back to the property. The system and method described herein place the casino staff at the beck and call of the player.

For the casino property application, the user profile is provided by the casino property and may be managed by the casino property. The user profile for a particular player may include information such as cocktail preferences, dining preferences, entertainment preferences, gaming preferences, and opt-out preferences. The handset can be used to gain VIP admissions to clubs and shows, and even room access.

In the casino property embodiment, the carriers will need to provide location information. In certain instances, such as within a building, GPS information may be more difficult to obtain, and a Wi-Fi network may be needed within the casino property, e.g. gaming zones and high roller suites.

To accommodate the user, a handset may be loaned to the user. The type of handsets that are loaned must possess a user interface (UI) that is attractive to the user. However, there may be resistance to using a new handset, when the user has invested so much time in understanding the existing UI on the user's current handset. Therefore, to accommodate the type of user not wishing to switch handsets, then the handset must be configured to receive one or more software programs, e.g. Java applets, which reside on the handset, and provide the functionality described above.

For illustrative purposes only, a dual mode handset is selected that includes COMA, EV-DO and Wi-Fi technology. The handset is GPS enabled. Wi-Fi technology and related triangulation technologies are used in certain locations where GPS may not provide sufficient accuracy. For example, it may desirable to send a high roller a targeted message when the high roller is at the Bar telling them that they qualify for a $500 credit, or they have "won" a free meal or a suite upgrade. Additionally, the handset may have a large storage component that stores user specific information that is triggered based on location and/or user requests. Thus, a desirable and targeted video message can play after the user has been sitting at the Bar for five minutes, and this message may be pre-loaded on the handset.

The handset may also be programmed in English or the whale's language of origin, e.g. Japanese, Mandarin, Korean, Arabic, Farsi, etc. The interface may be modified to include concierge information, and point of interest (POI) information. Room service and similar casino services can also be programmed into the handheld device.

In the illustrative casino property embodiment, player tracking information is not shared with another casino property and is not used for data mining by the Carrier because this will destroy the trust relationship that is being developed with the player and the casino property. Thus, it is of the utmost importance that this information not be accessible by a competing casino property.

Consumer Application

The consumer application may reside in either the client-server network architecture or the P2P network architecture. However, because of the viral nature of P2P networks and because of the desire for various entities to maintain the confidentiality of their information, a distributed solution such as a P2P is likely the preferred architecture.

In the illustrative consumer oriented embodiment, personalization is performed by the user. Generally, the profile is generated using a browser on a personal computer. With the tools described, each user can create a tailored user profile. The user profile can include information such as preferred dining preferences, hobbies, banking preferences, shopping preferences, and opt-out preferences.

In the consumer oriented embodiment, the user can identify specifics associated with the user's service plan. For example, the user may have disabled web browsing because of the challenges associated with Web surfing on a handset. Thus, the user service plan may only support voice calls, and SMS messages. For this particular user, the user profile may be configured to send targeted SMS messages. Preferably, the advertiser pays for the cost of the SMS message.

For the consumer oriented embodiment, one goal is to minimize the need for network modifications. Our goal is to provide an offering to carrier or service provider in which the user can configure their handset in a manner consistent with the actions performed by a highly targeted Mobile Virtual Network Operator (MVNO), except the embodiment adds a location component, user profiles and virtual agents.

Thus, the illustrative tools are able to simulate providing a user-defined MVNO handset that is adaptable. So, if a user starts with voice and SMS, MMS and obtains targeted messages that are limited by screen resolution and functionality of the handset, the user may wish to upgrade handsets and upgrade service features to obtain the more desirable targeted advertising. For example, coupon promotion may accommodate the advertisers and carriers business model, so a better promotion may be received on a more sophisticated handset.

It is to be understood that the foregoing is a detailed description of illustrative embodiments. The scope of the claims is not limited to these specific embodiments or examples. Therefore, various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A method for communicating a targeted message to a particular user, the method comprising:
   generating a first user profile by accessing a first node that monitors a plurality of historical user transactions at a particular location;
   receiving the first user profile at a merchant node;
   receiving a second user profile that is generated directly by the particular user;
   enabling the merchant node to access the second user profile;
   enabling a wireless device associated with the particular user to communicate with the merchant node;
   enabling the particular user accessing the wireless device to opt-in to provide location information to a location networked component;
   monitoring the wireless device with the location networked component to determine the location of the wireless device;
   communicating a targeted message to the wireless device from the merchant node based on a combination of the location of the wireless device, the first user profile, and the second user profile;
   enabling the wireless device to perform a transaction associated with the targeted message; and
   completing the transaction associated with the targeted message with the wireless device.

2. The method of claim 1, further comprising updating at least one of the first user profile and the second user profile based on a user response to the message sent to the wireless device.

3. The method of claim 1 wherein the second user profile is configured to be generated by accessing a search engine user profile.

4. The method of claim 1, further comprising sending messages to the wireless device when the wireless device is inside a store.

5. The method of claim 1, wherein the message includes a coupon for completing a coupon based transaction.

6. The method of claim 1, wherein the second user profile is stored on the wireless device or a personal computer of the particular user.

7. The method of claim 1, wherein the second user profile includes at least one member selected from a group consisting of dining preferences, banking preferences, shopping preferences, in-store preferences, and opt-out preferences.

8. The method of claim 1, wherein the message includes at least one of a SMS and a MMS message.

9. A system for communicating a targeted message to a particular user, the system comprising:
   a first node that monitors a plurality of historical user transactions at a particular location;

a first user profile associated with a particular user, wherein the first user profile is generated by accessing the first node;

a merchant node that accesses the first user profile;

a second user profile generated directly by the particular user;

a user wireless device associated with the particular user that communicates with the merchant node;

a location networked component that monitors a location of the user wireless device when a user opts-in to provide location information;

a targeted message communicated to the user wireless device from the merchant node based on the first user profile, the second user profile, and the location of the wireless device; and a transaction associated with the targeted message performed with the user wireless device.

10. The system of claim 9, wherein at least one of the first user profile and the second user profile are updated based on a user response to the message sent to the wireless device.

11. The system of claim 9 wherein the second user profile generated by accessing a search engine user profile.

12. The system of claim 9, wherein the message is sent to the wireless device when the wireless device is inside a store.

13. The system of claim 9, wherein the message includes a coupon for completing a coupon based transaction.

14. The system of claim 9, wherein the second user profile is stored on one of the wireless device and a personal computer of the particular user.

15. The system of claim 9, wherein the second user profile includes at least one member selected from a group consisting of dining preferences, banking preferences, shopping preferences, in-store preferences, and opt-out preferences.

16. The system of claim 9, wherein the message includes at least one of a SMS and a MMS message.

17. A system for communicating a targeted message to a particular user, the system comprising:

a first node configured to monitor a plurality of historical user transactions at a particular location;

a first user profile associated with a particular user, wherein the first user profile is configured to be generated by accessing the first node;

a merchant node configured to access the first user profile;

a second user profile configured to be generated directly by the particular user;

a user wireless device associated with the particular user that is configured to communicate with the merchant node;

a location networked component configured to monitor a location of the user wireless device when a user opts-in to provide location information;

a targeted message configured to be communicated to the user wireless device from the merchant node based on the first user profile, the second user profile, and the location of the wireless device; and a transaction associated with the targeted message, wherein the transaction is configured to be performed with the user wireless device.

18. The system of claim 17, wherein at least one of the first user profile and the second user profile are updated based on a user response to the message.

19. The system of claim 17, wherein the second user profile configured to be generated by accessing a search engine user profile.

20. The system of claim 17, wherein the second user profile is stored on one of the wireless device and a personal computer of the user.

21. The system of claim 17 wherein the message includes a coupon for completing a coupon based transaction.

* * * * *